United States Patent
Eibl et al.

(10) Patent No.: US 6,465,170 B2
(45) Date of Patent: Oct. 15, 2002

(54) METHOD FOR DEPLETING VIRAL AND MOLECULAR PATHOGENS IN A BIOLOGICAL MATERIAL

(75) Inventors: Johann Eibl, Vienna (AT); Friedrich Dorner, Vienna (AT); Noel Barrett, Klosterneuburg (AT); Gerhard Polsler, Vienna (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/934,330

(22) Filed: Aug. 20, 2001

(65) Prior Publication Data

US 2002/0018985 A1 Feb. 14, 2002

Related U.S. Application Data

(63) Continuation of application No. 09/445,862, filed as application No. PCT/AT98/00143 on Jun. 10, 1998.

(51) Int. Cl.[7] ............ A01N 1/02; C12N 5/00; C12N 5/08; A61K 39/42; C02F 1/38
(52) U.S. Cl. ............ 435/2; 435/325; 435/372; 424/159.1; 210/782
(58) Field of Search ............ 435/2, 325, 372; 424/159.1; 210/782

(56) References Cited

U.S. PATENT DOCUMENTS 5,773,277 A * 6/1998 Hashimoto et al.

FOREIGN PATENT DOCUMENTS

JP 355000304 * 1/1980

* cited by examiner

*Primary Examiner*—Christopher R. Tate
*Assistant Examiner*—Randall Winston
(74) *Attorney, Agent, or Firm*—Heller Ehrman White & McAuliffe

(57) ABSTRACT

A method for depleting viral and molecular pathogens in a biological material containing one or several biological substances to be recovered is disclosed, wherein the biological material is admixed with an organic solvent, the solvent-admixed biological material is contacted with an ion exchanger, wherein the pathogens are adsorbed on the ion exchanger material, and at least one of the biological substances to be recovered does not interact or interacts only slightly with the ion exchanger, and the ion exchanger with the pathogens adsorbed thereon is sesparated from the biological material, a virus-depleted preparation of the biological substance being recovered.

24 Claims, No Drawings

METHOD FOR DEPLETING VIRAL AND MOLECULAR PATHOGENS IN A BIOLOGICAL MATERIAL

This application is a continuation of application Ser. No. 09/445,862, filed May 18, 2000, which is a 371 of PCT/AT98/00143, filed Jun. 10, 1998.

The invention relates to a method for depleting viral and molecular pathogens in a biological material containing one or several biological substances to be recovered.

The production of therapeutic proteins and preparations, in particular of immunoglobulin, by extraction from human or animal tissues or liquids, such as blood or plasma, as well as from continuously growing transformed mammalian cells frequently carries the risk of a potential contamination by pathogens, such as viruses, virus-like particles or prions. Therefore, measures must be taken to prevent any pathogens possibly present from being transmitted to human beings.

Human blood or plasma, respectively, may e.g. contain viruses causing diseases such as AIDS, hepatitis B or other hepatitis diseases. With plasma proteins derived from plasma pools the risk of transmitting infectious agents, such as viruses, is very low because of the selection of blood or plasma donations and the production method. Suitable measures, such as excluding high-risk blood donors from donating blood as well as analyzing blood or plasma donations which make it possible to identify infectious donations and exclude them from further distribution, do allow an elimination of most of the infectious donations, yet in most instances not all can be found. Existing assaying systems for detecting infectious viruses in biological materials cannot always completely eliminate concerns regarding a potential transmission of pathogens, since on account of the broad spectrum of infecious pathogens existing it is impossible to assay the starting material for all viruses or molecular pathogens that may be present in a sample. Moreover, most of the tests do not identify the virus itself, but rather identify antibodies developed against that virus so that during the so-called "diagnostic window" a detection of a contamination is not possible. For some groups of viruses, moreover, a reliable or sufficiently sensitive detection method does not exist. Although newly developed assaying methods, in particular nucleic acid amplification methods, such as, e.g., PCR, are highly sensitive and specific, they can only be applied for pathogens whose nucleic acid sequence is known. In those cases in which the human pathogens are known yet a sensitive method of detecting them does not exist, there remains the doubt that a negative result is obtained merely on account of a too low virus content which is below the sensitivity limit of the assaying system.

Therefore, specific removal and/or inactivation methods for depleting viruses have been developed for the production of pharmaceutical and therapeutic products so that infectious particles are no longer to be expected in the final product.

Various inactivation methods are based on a physical-chemical treatment by means of heat and/or chemicals. The methods particularly used are the thermal treatment, pasteurizing, treatment of the protein solution with β-propiolactone and UV light, treatment with a combination of a solvent and a detergent (so-called S/D method) or exposing the protein solution to light after the addition of a photodynamic substance. With these methods, a virus inactivation of up to $10^6$ log steps has been reached. The efficiency of the inactivation method may, however, vary depending on the type of virus present. Although S/D-treated blood products are considered safe in terms of a transmission of HCV, HBV or HIV, non-enveloped viruses, such as HAV or parvovirus, are not inactivated by these methods (Prowse C., Vox Sang. 67 (1994), 191–196).

With biological products, heat treatment methods preferably are carried out either in solution (EP-0 124 506), in the dry state (EP-0 212 040 or WO 82/03871) or in the moistened state (EP-0 324 729). This may often result in losses because of the thermolability of many biological substances.

The type of the inactivation method used may also have an influence on the products, and a stabilisation to minimize the loss of protein thus frequently is required. Moreover, some inactivation methods must be followed by purification steps so as to remove chemicals added.

Methods for virus depletion particularly include chromatographic methods, filtration of protein solutions via a membrane filter, or adsorption of viruses on a solid phase and subsequent removal of the solid phase, as described in EP-0 679 405. However, it has been found that although the treatment with a solid phase, such as, e.g., with Aerosil®, does allow for a removal of HIV up to 4 log steps from an immunoglobulin-containing solution, the loss of IgG may be up to 42% (Gao et al., Vox Sang. 64 (1993), 204–209). With such high losses, such a method appears rather unsuitable for application on a large technical scale.

A widely used chromatographic method for isolating biological substances is anion exchange chromatography. The possibility of depleting viruses by this separation method has also been described in the literature. For instance, virus depletion at an anion exchange chromatography for purifying vWF under conditions under which vWF, yet not the virus, binds to the anion exchanger has been examined (Burnouf-Radosevich, Vox San. 62 (1992), 1–11). By thoroughly washing the column prior to elution, depending on the respective virus, it was possible to recover vWF with a virus depletion of from 1.5 to 5 powers of ten.

Zolton et al. (Vox Sang. 49 (1985), 381–389) examined the virus depletion rate in case of anion exchange chromatography for purifying gamma-globulins under conditions under which gamma-globulins do not bind to an anion exchanger. In these methods, DEAE Sepharose was used as anion exchanger at a pH of 7.5. The infectivity of a starting solution to which hepatitis B virus had been admixed could be eliminated by means of this anion exchange chromatography. By this experiment, a depletion of the hepatitis B virus by the factor 3000 was effected. However, nothing could be said about the depletion rate of other viruses at pH 7.5. What was interesting is that at a pH of below 7.2, viruses appeared in the effluent of the anion exchanger, so that this method generally has been considered not to be applicable in the neutral or weakly acidic pH range.

EP 506 651 describes a multi-step method of recovering a preparation containing IgA, IgG and Transferrin, a reduction of the virus titer having been obtained in each individual method step. During the extraction and precipitation step with 12% ethanol, a virus reduction by a factor of $10^5$ could be attained. During the adsorption step, the proteins were bound to an anion exchanger, washed, and eluted again. With this step, virus reduction was at a factor of $10^3$.

Burnouf (Dev. Biol. Stand. 81 (1993), 199–209) reported that during a purification of factor VIII, parainfluenza virus and HIV-1 could be depleted by 4 and 3 powers of ten, respectively, by means of an anion exchange step. When purifying vWF via anion exchange chromatography, a depletion rate of PRV (porcine pseudorabies virus) of 5 log steps has been reported.

Mitra et al. (Curr. Stud. Hematol. Blood Transfus. 56 (1989), 34–43) show that when purifying IgG from plasma according to the plasma fractionating scheme of Cohn-Oncley by a sequence of precipitating steps in the presence of certain concentrations of ethanol and defined pH values in the cold (–5° C.), a virus depletion of >5 and >8 log steps, respectively, of murine C-virus and HIV, respectively, could be obtained. In this paper it is also reported that a 25% ethanol solution at a physiological pH could be highly virucidal. According to Mitra et al., however, a combination of the ethanol treatment with an ion exchange chromatography is neither shown nor suggested.

Hamman et al. (Vox Sang. 67 (1994), 72–77) show that in the course of producing a factor VIII concentrate, a depletion of the virus activity or virus concentration, respectively, of merely 1 to 2 log steps can be attained by means of an ion exchange chromatography.

Therefore, there exists a demand for an industrially applicable method for a guaranteed separation of viruses from protein solutions so as to reduce the risks of infectivity for patients who are treated with pharmaceutical or therapeutical preparations of animal or human origin or prepared from cell cultures by a genetical engineering method.

Likewise, there is a demand for virus-safe, pathogen-free biological products in which it is already ensured by their preparation method that no pathogen is transmitted and that the method is gentle enough so as to leave the biological activity of the products largely unaffected.

Thus, it is an object of the present invention to provide an improved method of depleting viral and molecular pathogens in a biological material.

According to the invention, this object is achieved by a method of the initially described kind which is characterized in that the biological material is admixed with an organic solvent, the biological material with the organic solvent admixed thereto is contacted with an ion exchanger, wherein the pathogens are adsorbed on the ion exchanger material, and at least one of the biological substances to be recovered does not interact or interacts only slightly with the ion exchanger material, and the ion exchanger with the pathogens adsorbed thereon is separated from the biological material, a virus-depleted preparation of the biological substance being recovered.

Surprisingly it has been found that in the presence of the organic solvent, the reduction factor of the ion exchange step was substantially increased as compared to that described in the prior art. Thus, Hamman et al. (supra) found a reduction factor of merely 1 log step in the ion exchange step.

Therefore, it could not be expected that in a single-step method, i.e., an adsorption method, a high reduction factor could be expected without further elution. Likewise, it has been surprising that the presence of the solvent substantially changes the adsorption specificity of the ion exchanger, whereby pathogens are bound, while biological substances, in particular proteins, substantially remain unbound. Thus, with the method of the invention it has been possible e.g. for HAV to attain a reduction factor of >5.95 log steps, which corresponds to a complete depletion, while in contrast thereto Hamman et al. attained a reduction factor of merely 1 log step for HAV by means of an ion exchange step.

It has been known that a depletion treatment with 12% ethanol can assist in the virus reduction, yet it has been highly surprising that an organic solvent is also suitable to be applied simultaneously with an ion exchange treatment for virus depletion.

Within the scope of the present invention it has been shown that, particularly with the anion exchange chromatography or the adsorption on an anion exchanger, respectively, particular depletion rates can be achieved, preferably in combination with materials based on carbohydrates or synthetic polymers, such as, e.g. DEAE-Sephacel®, DEAE-Sephadex®, DEAE-Sepharose CL6B®, DEAE-Sepharose Fast Flow®, QAE-Sephadex®, Q-Sepharose Fast Flow®, Q-Sepharose High Performance®, Q-Sepharose Big Beads® (all from Pharmacia); DEAE-Tris-Acryl®, DEAE-Spherodex®, Q-Hyper-D® (all from Sepracor); Macroprep DEAE®, Macroprep Q® (all from BioRad); DEAE-Toyopearl®, QAE-Toyopearl®, Toyopearl Super-Q® (all from Tosohaas); Protein PAK DEAE® (Waters); Fractogel EMD-TMAE®, Fratogel EMD-DEAE®, Fractogel EMD-DMAE®, Licrospher 1000 TMAE®, Licrospher 1000 DEAE® and Licrospher 4000 DMAE® (all from MERCK). Particularly preferred (primarily when processing immunoglobulin) is an anion exchanger of the DEAE type, in particular of the DEAE-Sephadex type.

Subsequently, the pathogens adsorbed on the ion exchanger are removed by separating the ion exchanger/pathogen complex from the biological material. In this manner, the adsorbate is immediately separated from the biological material in a simple manner and without treatment with an elution buffer. Preferably, the complex is separated by passing the biological material through a permeable filter, in particular a deep bed filter. Separation of the complex may also be effected by sedimentation, in particular centrifugation. Preferably, separation of the ion exchanger is also effected in the presence of the solvent.

Within the scope of this invention, by biological substances, substances of biological origin are meant, which are recovered e.g. from body fluids, such as blood or plasma, or may be isolated from the culture supernatants of recombinant cells, wherein these biological substances to be recovered within the scope of the present invention or whose virus contamination is to be depleted, respectively, may particularly be used therapeutically, prophylactically or diagnostically or as pharmaceutical preparations, respectively. These biological substances may, e.g., be proteins/peptides, carbohydrates or lipids, in particular biologically active substances, such as immunoglobulins or blood factors. Yet also other classes of substances which may be formed by prokaryotic or eukaryotic cells are to be summarized as "biological substances".

The recovery of virus-depleted preparations of the biological substances from the supernatant of the adsorbate or from the filtrate, respectively, commonly is effected by further processing or purification of the biological substances or fractions of the biological material, respectively, precipitations, chromatographic purification methods, a filtration, diafiltration, formulation i.a. being effected.

Within the scope of the present invention, the biological material may be a plasma fraction, an immunoglobulin-containing plasma fraction, preferably COHN fraction II+III, a plasma protein-containing fraction comprising blood factors, such as, e.g., factor II, factor VII, factor VIII, factor IX, factor X, factor XI, protein C, protein S, vWF, a concentrate comprising one of the said blood factors, a supernatant of a hybridoma cell line, a cell culture supernatant of transformed or infected mammalian cells or an extract of an animal or human tissue. The parameters for carrying out the method will each be adapted to the type and nature of the biological material used and to the contaminating pathogens possibly present therein. The optimal parameters, such as pH, temperature, period of incubation for carrying out the method, type of organic solvent used in the method according to the invention, in dependence on the type of pathogen, the specificity of the ion exchanger, and the nature of the biological material used (purity of solution, protein concentration in the solution) may be found by the skilled artisan on the basis of his general knowledge.

The method according to the invention is particularly suitable to deplete molecular and/or viral pathogens in a biological material, viral pathogens both of the group of lipid-enveloped and of the group of non-lipid-enveloped viruses being effectively removed. Among them are in particular viruses such as HAV, HBV, HCV, HGV, HEV, HDV, HIV, CMV or parvovirus.

Within the scope of the present invention, by organic solvents in particular such solvents are to be understood which do not trigger any substantial denaturing processes when being admixed with the biological materials under the conditions chosen. Among them are particularly solvents, such as methanol, ethanol, or other biologically compatible alcohols.

The optimal concentration of the respective solvent—just like slight deviations in the optimal chromatographic conditions, which may possibly be caused by the presence of the solvent—will be easy to be determined for any skilled artisan by simple experiments. In general, the solvent will be employed at a concentration of from 5 to 20% by volume, preferably at a concentration of from 10 to 15% by volume, in particular at a concentration of approximately 12 to 14% by volume.

Preferably, a mono- or polyvalent alcohol is employed as the organic solvent, ethanol being particularly preferred. According to the invention, particularly preferred ethanol concentrations are between 12 and 14% by volume, in particular between 13 and 14% by volume.

Preferably, the ion exchange treatment is carried out at low temperatures, temperatures of below 10° C. or below 5° C. being preferred. It has been shown that the anion exchange treatments are particularly suitable at a temperature of between 0 and −10° C. for the method according to the invention.

It has also been shown that the method according to the invention, in contrast to prior art reports, in particular in contrast to the results of Zolton et al. (1985), can also be successfully employed at pH values of below 7.5 or 7.2, respectively, i.e. in the neutral and acidic range, respectively.

A preferred method variant of the method according to the invention thus consists in that the treatment of the biological material with the ion exchanger, in particular with the anion exchanger, is carried out at a pH of from 5.6 to 7.2, preferably between 6.0 and 6.4, in particular at pH 6.2.

Treatment of the aqueous solution of the biological material with the anion exchanger preferably is carried out for a period of time of from 1 minute to 20 hours, in particular for 4 to 8 hours, wherein incubation may either be effected in the batch method or in a continuous flow system.

With the method according to the invention, a biological material may be obtained which is safely free from molecular and/or viral pathogens, wherein the pathogens are substantially completely removed. Thus, depending on the added ethanol concentration, a substantially complete virus removal has been found. By the single-step method according to the ivnention, a pathogen reduction factor of preferably >5.5 log steps, particularly preferred >7.0 log steps, is attained.

The optimal adsorption conditions during the ion exchange chromatography may easily be optimized by any skilled artisan by referring to the teaching of the present invention, depending on the biological substance to be recovered and on the virus to be adsorbed, respectively, and depending on the respective organic solvent used.

The present method is also excellently suited for a combination with further pathogen-inactivating or pathogen-depleting steps, such as thermal and/or detergent treatment, radiation treatment or filtration, nanofiltration according to Austrian application A 780/96 being particularly preferably combinable with the method according to the invention.

The present method is particularly suited for producing immunoglobulin preparations, yet it may also be specifically employed for the recovery of pharmaceutical preparations, blood factors, such as factor II, factor IIa, factor VII, factor IX, factor X, protein S, protein C or vWF.

The present invention will be explained in more detail by way of the following examples, without, however, being restricted thereto.

EXAMPLES

Example 1

Virus Depletion in IgG-containing Solutions (at Present Considered by Applicant to be the Best Mode of Carrying out the Invention)

An immunoglobulin-containing COHN-fraction II+III was adjusted with ethanol to a final concentration of 10% to 14%, each, and the solution was brought to a temperature of −3° C. to −1° C. Subsequently, the solution was admixed with the test viruses stated in Table 1. Per g of protein, 0.5 g of DEAE-Sephadex A-50 were admixed, the pH was adjusted at 6.2±0.1, and incubation was effected by keeping constant the temperature and the pH for 6 hours under stirring. Subsequently, the exchanger suspension was removed by deep bed filtration, and the virus titer in the filtrate was determined. The virus depletion rate, expressed as the decrease of the infectious virus particles in powers of ten, is summarized in Table 1 and was determined by means of virus titration or PCR. As is apparent from this table, this method—depending on the test virus used—leads to a depletion by 2 to more than 6 powers of ten. The yield of IgG in the supernatant was >70%. In control experiments in which the incubation of the test virus was carried out analogously without the addition of the anion exchanger, no virucidal effect of the ethanol could be found under these conditions.

TABLE 1

IgG i.v. OA1 Method
DEAE-Sephadex and Filtration

| Ethanol | 10% | 11% | 12% | 13% | 14% |
|---|---|---|---|---|---|
| Yield | 100% | 100% | 100% | 100% | 97% |
| | | | IRF[log] | | |
| PRV | n.d. | n.d. | 2.95 | >5.44 | >5.40 |
| MVM | 2.76 | 3.73 | >6.76 | n.d. | >6.27 |
| TBE | n.d. | n.d. | 5.00 | 5.96 | n.d. |
| BVDV | n.d. | n.d. | 1.80 | 2.61 | >4.35 |
| HCV | n.d. | >3.94 | >5.32 | n.d. | n.d. |
| HAV | n.d. | 3.91 | >5.95 | n.d. | n.d. |
| HGV | n.d. | n.d. | 4.03 | n.d. | n.d. |
| HIV | n.d. | n.d. | >4.30 | n.d. | n.d. |
| ERV | n.d. | n.d. | >5.10 | n.d. | n.d. |

PRV = Pseudorabies virus
MVM = Minute Virus of Mice/parvovirus
TBE = Tick-borne encephalitis virus
BVDV = Bovine diarrhea virus
HCV = Hepatitis C virus
HAV = Hepatitis A virus
HGV = Hepatitis G virus
HIV-1 = Human Immunodeficiency Virus-1
ERV = Equine rhinopneumonitis virus
n.d. = not determined Example 2

Depletion of Parvovirus from IgG-containing Solutions

An immunoglobulin-containing COHN fraction III having an ethanol content of 12% was admixed in an analogous manner, as described in Example 1, with parvovirus B19. The total load in the B19-admixed starting material was $10^{11.3}$ DNA copies/ml. The DEAE-Sephadex adsorption step with subsequent filtration was carried out as described in Example 1. DNA copies/ml were determined in the filtrate by means of PCR, as described in Austrian application A 780/96. No parvovirus-specific DNA could be detected in the filtrate. Taking into consideration the detection limits, a virus reduction factor of >7.4 log steps was achieved with the method according to the invention.

What is claimed is:

1. A method for depleting viral and prion pathogens in a biological material comprising at least one biological substance, wherein the method comprises
   mixing the biological material with an organic solvent to obtain a solvent-containing biological material,
   contacting the solvent-containing biological material with an ion exchanger to adsorb pathogens on the ion exchanger, wherein at least one biological substance is at least substantially non-interactive with the ion exchanger, and
   separating the ion exchanger from the biological material, thereby recovering a pathogen-depleted preparation comprising at least one biological substance.

2. A method as set forth in claim 1, wherein said ion exchanger is an anion exchanger.

3. A method as set forth in claim 2, wherein said anion exchanger is a DEAE-type anion exchanger.

4. A method as set forth in claim 3, wherein said DEAE-type anion exchanger is DEAE-Sephadex.

5. A method as set forth in claim 1, wherein said organic solvent is used at a concentration of from 5 to 20% (v/v).

6. A method as set forth in claim 1, wherein said organic solvent is used at a concentration of from 10 to 15% (v/v).

7. A method as set forth in claim 1, wherein said organic solvent is used at a concentration of from 12 to 14% (v/v).

8. A method as set forth in claim 1, wherein said organic solvent is selected from the group consisting of monovalent and polyvalent alcohols.

9. A method as set forth in claim 1, wherein said organic solvent is ethanol.

10. A method as set forth in claim 1, wherein said biological material is incubated with said ion exchanger at a temperature of below 10° C.

11. A method as set forth in claim 10, wherein said temperature is below 5° C.

12. A method as set forth in claim 10, wherein said temperature ranges between 0 and -10° C.

13. A method as set forth in claim 1, wherein said biological material is incubated with said ion exchanger at a pH of between 5.2 and 7.2.

14. A method as set forth in claim 13, wherein said pH ranges between 6.0 and 6.4.

15. A method as set forth in claim 13, wherein said pH is approximately 6.2.

16. A method as set forth in claim 1, wherein said biological material is incubated with said ion exchanger for 1 to 20 hours, wherein the biological material is incubated by a batch approach or a continuous flow approach.

17. A method as set forth in claim 16, wherein said incubation is for 4 to 8 hours.

18. A method as set forth in claim 9, wherein said ethanol has a concentration of from 5 to 20%.

19. A method as set forth in claim 9, wherein said ethanol has a concentration of from 10 to 15%.

20. A method as set forth in claim 9, wherein said ethanol has a concentration of from 12 to 14%.

21. A method as set forth in claim 1, wherein said biological substance is a blood factor.

22. A method as set forth in claim 1, wherein said separating of said ion exchanger is performed by filtration.

23. The method according to claim 1, wherein the pathogen is a virus.

24. The method according to claim 1, wherein the pathogen is a prion.

* * * * *